United States Patent [19]

LeFord

[11] Patent Number: 5,731,501
[45] Date of Patent: Mar. 24, 1998

[54] INBRED MAIZE LINE CG4NU15

[75] Inventor: Duane LeFord, Owatonna, Minn.

[73] Assignee: Novartis Corporation

[21] Appl. No.: 671,884

[22] Filed: Jun. 28, 1996

[51] Int. Cl.$^6$ .............................. A01H 5/00; A01H 4/00; A01H 5/10; C12N 5/04

[52] U.S. Cl. ............................................................ 800/200

[58] Field of Search .................. 800/200, 235, 800/250, DIG. 56; 435/412, 424, 430, 430.1; 47/58, DIG. 1

*Primary Examiner*—David T. Fox
*Assistant Examiner*—Thanda Wai
*Attorney, Agent, or Firm*—Thomas Hoxie

[57] ABSTRACT

An inbred maize line, designated CG4NU15. This invention thus relates to the plants and seeds of inbred maize line CG4NU15 and to methods for producing maize plants by crossing inbred line CG4NU15 with itself or with another maize line. This invention further relates to hybrid maize seeds and plants produced by crossing inbred line CG4NU15 with another maize line.

17 Claims, No Drawings

5,731,501

1

INBRED MAIZE LINE CG4NU15

FIELD OF THE INVENTION

This invention is in the field of hybrid maize (Zea mays L.) plant breeding, specifically relating to the inbred maize line designated CG4NU15.

BACKGROUND OF THE INVENTION

Of all the crops produced by U.S. farmers, maize is the crop that has the most economic value. Maize is utilized as livestock feed, as a basis for human consumption, as raw material for industry and as raw material for the production of ethanol. The primary use of farmer produced field maize is for livestock feed. This includes feed for hogs, beef cattle, dairy cows and poultry.

Human consumption of maize includes direct consumption of sweet maize and as snacks after extruder cooking, ground maize eaten as grits, maize meal and maize flour. Maize oil is also used as a high grade cooking oil, salad oil or in margarine. Maize is used in the production of some starches and syrups. Another important use is in the production of sweeteners used in soft drinks.

The wet-milling and dry-milling processes also produce maize starch and maize flour that have applications in industry. Some of these uses include building materials, the paper industry, textiles and starches.

The seed of inbred maize line CG4NU15, the plant produced by the inbred seed, hybrid seed produced from the crossing of either inbred to another inbred, the hybrid maize plant grown from said seed, and various parts of the inbred and hybrid maize plant can be utilized for human food, livestock feed, and as a raw material in the industry.

Maize Breeding

Among the major reasons for the economic importance of maize and the large acreages planted to the crop are the hybridization of the maize plant and the continued improvement, by researchers, of the genetic stock that is used to produce the seed grown by farmers. This process has been on-going since its beginning in the early part of the century. The average bushel per acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

The physical structure of the maize plant provides the maize breeder with opportunities either to cross a plant with another plant or to self-pollinate a given plant. Since the male inflorescence (the tassel) and the female inflorescence (the ear) are physically separated from each other on the plant, the breeder has the ability to mate plants as desired with ease. Similar physical manipulations are used both for cross-pollinating and for self-pollinating a maize plant. The silks (stigmae of maize female florets) are protected from pollination until pollen is collected from the male inflorescence. For cross-pollination, pollen from one plant is distributed on the silks of another plant, while for self-pollination, pollen from a plant is distributed on silks of the same plant. Sib-pollination is a type of cross-pollination in which both plants are closely related genetically. Cross pollinating and self-pollinating techniques are used in the development of inbreds which, when crossed, produce seed of commercially available maize hybrids. Self-pollination and sib-pollination increase the level of inbreeding in progeny plants, leading to fixation of alleles. With continued inbreeding comes a large reduction in vigor and productivity. This phenomenon is know as inbreeding depression. The progeny from the crossing of two inbred lines is a first generation ($F_1$) hybrid, which has better productivity and agronomic characteristics than either of the inbred parents. This phenomenon is called hybrid vigor or heterosis. Heterosis is reduced markedly In succeeding generations ($F_2$, $F_3$, etc.), making it economically justifiable for the farmer to obtain $F_1$ seed each year. As a result, the hybrid maize seed industry benefits both farmers and producers of hybrid maize seed.

Maize is a highly variable species. For hundreds of years, maize breeding consisted of isolation and selection of open-pollinated varieties. Native Americans evolved many different varieties since the domestication of maize in prehistory. During the course of the nineteenth century, North American farmers and seedsmen developed a wide array of open-pollinated varieties, many of which resulted from an intentional or an accidental cross between two very different types of maize: the Southern Dents, which resemble varieties still grown in Mexico, and the Northern Flints, which seem to have moved from the Guatemalan highlands into the northerly parts of the United States and into Canada. The open-pollinated varieties which were developed during this time were maintained by selection of desirable ears from within the variety for use as foundation seed stock. The only pollination control which was practiced to generate the seed was isolation of the seed crop from pollen from other varieties. Experimentation with inbreeding in open-pollinated varieties showed that it invariably led to a marked reduction in plant vigor and stature, as well as in productivity.

In the early twentieth century, researchers discovered that vigor was restored when a line inbred from an open-pollinated variety was crossed to another, usually unrelated, inbred, and that the resulting hybrids were not only more uniform than open-pollinated varieties, but in many cases were more productive as well. Many of the inbreds developed from open-pollinated varieties were remarkably unproductive, however, which made $F_1$ seed quite expensive to produce in any volume. By the 1930's seedsmen were offering four-way or double crosses to growers. These consisted of a cross between two single crosses, which in turn were each crosses between two inbred lines. In this way, only a small quantity of single cross seed was required, and the seed sold to growers was produced on $F_1$ hybrids. Four-way crosses dominated the seed industry until the late 1950's, when three-way crosses were offered to growers, consisting of seed produced on a single cross hybrid with an inbred line as the pollinator. Through the efforts of public and private maize breeders, inbred lines were selected to be more productive and vigorous than the earlier selections from the open-pollinated varieties, and by the early 1970's, single cross seed was readily available to growers. Presently, the overwhelming majority of hybrid maize seed sold in the United States is single cross seed.

The method of hybridization in maize first involves the development of inbred lines. Inbred lines are commonly developed through some variation of pedigree breeding, wherein the plant breeder maintains the identity of each new line throughout the inbreeding process. To initiate the pedigree breeding process, the breeder may make an $F_1$ cross between two existing inbred lines which complement each other for traits for which improvement is desired, and which cross well with other inbreds from other genetic backgrounds to make commercial hybrids. The $F_1$ is selfed to provide $F_2$ seed, which is planted and selfed to produce the $S_2$ or $F_3$ generation. $S_2$ lines are planted ear-to-row, and self-pollinations are made within individual rows. Rows which do not provide a desirable phenotype are discarded. Selected ears are planted ear-to-row, and this process repeats until substantial homozygosity is attained, usually by the $S_6$ or $S_7$ generation. Once homozygosity is attained, the inbred can be maintained in open-pollinated isolations.

Maize breeders in general structure their efforts to take advantage of known heterotic patterns; that is, they use their knowledge of which inbreds make good hybrids with which other inbreds, and they ensure that genetic material from these heterotic pools does not cross over into opposing pools. A highly successful heterotic pattern in the United States corn belt has been to use lines from a population known as Iowa Stiff Stalk Synthetic crossed with lines having more or less of a Lancaster background to provide hybrids for growers (Lancaster was a relatively unimportant open-pollinated variety, until it was discovered in the early years of inbred/hybrid development that it provided an outstanding source of lines with good general combining ability). Other heterotic patterns have also been developed, primarily for the northern and southern regions of the United States. Breeders have understandably been reluctant to use competitive private company hybrids as source material, because, in such instances, usually it will not be known where derived lines fit in a heterotic pattern (Hallauer et al., "Corn Breeding", *Corn and Corn Improvement* pp. 463–564, (1988). As well, using competitors' hybrids as source germplasm risks the dispersal of existing heterotic patterns: many breeders feel that introducing, for example, Lancaster material into an Iowa Stiff Stalk background would lessen their ability to develop lines which could be crossed to Lancaster-derived inbreds. Unless it is known that a competitor's hybrid was genetically distinct from a breeder's own material, it is considered to be a more risky approach to improvement of a heterotic pool than utilizing known material.

While a maize breeder might anticipate that a source population is capable of providing a certain degree of variation, that variation first has actually to occur, and then to be identified by the breeder. Most variants are expected to fall between the parental values for any given trait; only very exceptional individuals will exceed the better parent (or be worse than the worse parent) for a trait. This is especially true when a trait is determined by a large number of genes, each having a relatively small effect on the trait. Most traits of interest to the maize breeder, including productivity, maturity, and stalk and root quality, are such traits. To complicate matters further, high negative correlations occur in maize between productivity, maturity, and stalk quality. A breeder may be able to improve yield, but at the expense of stalk quality or later maturity. The occurrence of an individual with a superior combination of traits is very rare. Even if the individual does occur in a sample of the source population, the breeder often lacks the resources required to identify that individual. Traits of low heritability, such as productivity, must be evaluated in several locations to be accurately evaluated. Only a very limited number of genotypes can be tested because of constraints upon resources. Thus, a breeder may miss the desired individual, simply because he cannot evaluate all genotypes produced by the source population. A valuable lesson was learned years ago about the expectation of the success of progeny improvement methods. The inbred Wf9 was developed in Indiana, and released to seed growers in the mid-1930's. Despite having several agronomic deficiencies, it became the most widely used inbred during the double-cross era of maize seed production. It naturally became the basis for numerous public improvement projects. Despite having abundant resources placed with the objective of developing an improved Wf9, no inbred from the public sector with a Wf9 background ever supplanted Wf9 in seed production fields. At the time of the initiation of these Wf9 progeny improvement programs, such an effort was obvious to try. However, it became apparent over the course of years that success from this effort was far from obvious, and Wf9 eventually was supplanted by unrelated lines in commercial production. A similar story can be told about A632, at one time the predominant seed line for Northern Corn Belt hybrids. Many public breeders tried to improve on A632, but no A632-derived line from the public sector achieved the prominence of A632, and it was eventually supplanted by a completely unrelated inbred. More recently, B73 improvement programs have been tried, but few B73-derived progenies have been commercially accepted.

These examples show clearly that, rather than being an obvious exercise in (for example) crossing the two best Iowa Stiff Stalk lines with each other, and reliably being able to pull out an even better progeny, maize breeding is inherently unpredictable. Breeders employ strategies taught by Hallauer et al and Meghji et al. crop science 24, 545–549 (1984) such as choosing the best available materials to provide populations, deriving progenies through a pedigree breeding scheme, and testing in replicated tests across environments, in order to maximize the likelihood of success, not to ensure it. Even restricting efforts to known heterotic patterns, a breeder can never be certain that a given cross will provide an improved inbred. The nature of heterosis is not at all well understood. No one knows why, for example, B73 X Mo17 was such an advance in productivity over previous hybrids. To say they are heterotic is uninformative: it merely describes what has been observed without explaining the phenomenon. Part of the uncertainty results from the mode of inheritance of many traits of interest, and the mathematics of genetically segregating populations. For example, the trait of chief interest in maize, productivity of marketable grain, is not simply inherited, but instead derives from the action of many genes of relatively small effect. This type of inheritance, known as quantitative inheritance, has been extensively studied from a theoretical standpoint, and certain aspects of the behavior of segregating populations can be mathematically predicted. One finding is that the probability of obtaining a specific homozygous inbred decreases exponentially with the number of segregating loci for a given trait R. W. Allard (*Principles of Plant Breeding,* John Wiley & Sons, New York, (1960) p.68) teaches that, from a population segregating at n loci, with each locus having only two variants, $2^n$ homozygous genotypes are possible. Thus, if a source population were segregating at only twenty loci, the probability of obtaining any given inbred genotype from this population is less than one in a million. The probability decreases very quickly with more heterozygous loci. Also, if there are loci with more than two variants, the number of possible homozygotes increases and the probability of retrieving a given inbred genotype decreases. The number of loci which affect the trait of gross productivity has been variously estimated at 10 to 1000. In addition, a breeder must pay attention to agronomic traits such as maturity, stalk quality, root quality, grain quality, resistance to diseases and insects, and many others, some of which appear to be negatively correlated with productivity. The total number of genetic loci in the maize genome has been conservatively estimated to be greater than $10^5$.

The objective of a plant breeder when developing a new inbred line of maize is to combine the highest number of desirable alleles into a single isolate as possible. No parent line contains all desirable alleles at all loci, and the breeder hopes to introgress a higher frequency of favorable alleles into resulting progenies. However, with the current state of the art, a breeder is generally not able to define which allele at any given locus is desirable, and for most traits of interest, he does not have information about which genetic loci are involved in influencing the trait. His primary tool to measure the genotypes of progenies is phenotypic evaluation. The phenotype of a plant is influenced both by its genotype and the environment in which it is grown, so the phenotypic measure of a plant is only an indirect measure of its genotype. When environmental effects are large relative to the genotypic effects, it is said that the trait has low heritability. The breeder must evaluate traits of low heritability in many different environments in order to be reasonably sure that he has an accurate estimate of the genotypic effect. Productivity of marketable grain is such a trait, according to years of breeding experience and numerous scientific publications.

The requirement of evaluating genotypes in different environments places serious restraints on the maize breeder in terms of the number of genotypes the breeder will be able to evaluate. The large number of possible genotypes, coupled with the small sample size from a segregating population, make it uncertain that a breeder will be able to invent a new maize inbred which is a measurable improvement over its parents. The invention of new inbred lines and of new hybrids is extremely important to the companies in the hybrid seed maize industry that have investments in research. Much effort is given to the research and development of these inbreds and hybrids. The breeding and selection of inbred lines is a highly specialized skill. It involves many years of inbreeding, skilled selection, correct statistical testing, and decision making.

Techniques involving the tissue culture of maize cells and plant parts has been developed to the point that it is now possible to regenerate plants from nearly all genotypes, by varying the culture media in which the cells or parts are cultured. Based upon experience with other inbreds with somewhat similar genetic background, it is anticipated that inbred maize line CG4NU15 will readily provide regenerable cells in culture of cells or plant parts.

SUMMARY OF THE INVENTION

According to the invention, there is provided a two novel inbred maize line, designated CG4NU15. This invention thus relates to the seeds of inbred maize line CG4NU15, to the plants of inbred maize line CG4NU15, and to methods for producing a maize plant produced by crossing the either inbred line CG4NU15 with itself or another maize line. This invention further relates to hybrid maize seeds and plants produced by crossing the inbred line either CG4NU15 with another maize line.

DEFINITIONS

This section will outline the definitions of terms used herein.

The following are traits evaluated in Table 1:

Plant height is self-explanatory.

Ear height is the height from the ground at the point of exsertion from the stalk of the highest ear.

Initial pollen is stated as number of days from planting to the first pollen shed observed in the variety.

Initial silk is stated as number of days from planting to the first silks observed in the variety.

Mid pollen is stated both as number of days and as heat units from planting to the date of full pollen shed observed in the variety. Heat units are calculated on a daily basis as ((Maximum temperature in degrees Fahrenheit—Minimum temperature in degrees Fahrenheit)/12)−50, with the constraint that temperatures above 86° F. are counted as 86° F., and temperatures below 50° F. are counted as 50° F.

Mid silk is stated as number of days and as heat units from planting to the full silking observed in the variety. Heat units are calculated as above.

Tassel size rating describes the size of the tassel, in which a rating of 1 indicates a small tassel and 9 indicates a large tassel.

Kernels per kilogram is self-explanatory.

Percent of large kernels is the percentage of kernels which pass through a $24/64$ inch round sizing screen but not through a $21/64$ inch round sizing screen.

Percent of medium kernels is the percentage of kernels which pass through a $21/64$ inch round sizing screen but not through an $18/64$ inch round sizing screen.

Percent of small kernels is the percentage of kernels which pass through a $18/64$ inch round sizing screen but not through a $33/128$ inch round sizing screen.

Percent of round kernels is the percentage of kernels which do not pass through a $13/64$ inch slot sizing screen.

Percent of discard kernels is the percentage of kernels which pass through a $33/128$ inch round sizing screen plus the percentage of kernels which do not pass through a $26/64$ inch round sizing screen.

Number of 80000 kernel units per hectare accounts for yield and and seed sizes, including discard seed.

The following traits are evaluated in Tables 2a through 2d:

Value. Value is a simple index which takes into account yield of a hybrid maize variety, market price for grain maize, and the cost of drying to storage moisture (15.5%). It is expressed in dollars per acre.

Yield (Bushels/Acre). Yield in bushels/acre is the actual yield of the grain at harvest adjusted to 15.5% moisture.

Percent Moisture. The percent moisture is the water content by weight of the grain at harvest.

Percent Erect. The percent erect, a measure of standability, is the percentage of plant stalks that are not broken below the ear at the time of harvest.

Percent Erect Push. Another measure of standability, this is the percentage of plant stalks that are not broken below the ear after having been manually pushed.

Harvest Roots. Harvest roots is a visual rating. It is based on the number of plants that are root-lodged (leaning from the vertical at an approximate 30° angle or greater) at the time of harvest. The ratings range from 1 to 9. a rating of 1 equals no plants root-lodged and a rating of 9 equals all plants root-lodged.

Percent Dropped Ears. The percent dropped ears is the percentage of plants whose ears have fallen to the ground at the time of harvest.

Intactness. Intactness is a visual rating based on the percentage of leaf and stalk matter remaining above the top ear at harvest. The ratings range from 1 to 9. A rating of 1 equals all matter remaining (intact) and a rating of 9 equals all matter gone or the stalk broken over just above the ear.

Percent Green or Staygreen. The percent green is the percentage of the total ear, leaf and stalk matter still green at the time of data collection, approximately physiological maturity.

Plant height is the height of the plant from the ground to the tip of the tassel.

Ear height is the height from the ground of the point of exsertion from the stalk of the highest ear.

The following traits are provided in the inbred description:

Plant height, ear height, number of primary tassel branches, leaf blade width, number of kernel rows, cob color, cob diameter, ear diameter, and ear length are self-explanatory.

Leaf attitude describes the manner in which leaves of an inbred variety of maize are arrayed on the plant.

Tassel branch shape describes how the tassel branches are arrayed in the male inflorescence.

Anthocyanin pigmentation in various plant parts (glumes, glume bands, anthers, silks, leaf sheaths, internodes, brace roots) describes the intensity of red or purple coloration in these plant parts.

Ear shape describes the amount of taper found in the ears, which can range from no taper (cylindrical shape of the ears), to much taper (conical ears).

Grain type describes the flintiness of the grain, which can range from fully flint kernel type to floury kernel type.

Flowering information describes the flowering time relative to appropriate check inbred lines of maize.

Flowering synchrony describes whether the plants of the inbred typically silk before pollen shed, silk at the same time as pollen shed, or silk after pollen shed.

DETAILED DESCRIPTION OF THE INVENTION

Inbred maize line CG4NU15 is a yellow semi-dent maize inbred line with superior characteristics and is a good parental line in crosses for producing first generation ($F_1$) hybrid maize. Inbred maize line CG4NU15 is a proprietary inbred of Ciba Seeds.

Inbred maize line CG4NU15 was selected for uniformity and agronomic traits using standard pedigree ear-row selection at Winterset, Iowa, Glidden, Iowa, and Kaunakakai, Hi. The source population of CG4NU15 was a single cross between two proprietary inbred lines. The two inbreds combined to make the source population differed widely in terms of maturity, germplasm background, disease resistances, and other traits. The inbred was evaluated as a line and in numerous crosses by the Bloomington Research Station and other research stations across the northern and central maize belt. Thus the line was evaluated for general and specific combining ability. Inbred maize line CG4NU15 is adapted to the north central maize belt and can be used advantageously in producing hybrids that are from approximately 95 day relative maturity to 110 day relative maturity based on the Minnesota Relative Maturity Rating System for harvest moisture of the grain. The inbred is a tall inbred with dark green leaves. It sheds pollen well but has deficiencies as a seed parent, and is preferred as the pollen line in hybrid production. This line produces relatively tall hybrids with high yielding ability for maturity, good grain quality, good stalk quality and average root quality.

Inbred maize line CG4NU15 has shown uniformity and stability for all traits as described in the following variety description information. It has been self-pollinated and ear-rowed a sufficient number of generations with careful attention paid to uniformity of plant type to insure relative homozygosity and phenotypic stability. The line has been increased by hand and in isolated fields with continued observations for uniformity. No variant traits have been observed or are expected in CG4NU15.

Inbred maize line CG4NU15 is slightly taller than average for lines of its flowering maturity, with ear placement approximately one-half the total plant height. It tends to produce slightly more than one ear per plant. The main ear tends to be longer than average for its flowering maturity, usually with twelve rows of large kernels. The ear is cylindrical. The silk color of CG4NU15 is green, the cob color is red, and the grain is a yellow flint-dent with average quality. Pollen shed occurs slightly before silking. The leaf color of CG4NU15 is medium green, and the leaf attitude is slightly above horizontal. Leaves are of medium width. The tassel of CG4NU15 has approximately six tassel branches, which are semi-drooping with respect to the main tassel axis, and the anthers are yellow. Pollen shed is good. All green plant parts are typically free of anthocyanin pigmentation.

CG4NU15 is resistant to northern corn leaf blight Race 1 (*Exserohilum turcicum*), resistant to southern corn leaf blight (*Bipolaris maydis*), intermediate in resistance to common rust (*Puccinia sorghi*), moderately susceptible to eyespot (*Kabatiella zeae*), resistant to common smut (*Ustilago maydis*), and moderately resistant to Stewart's wilt and leaf blight (*Erwinia stewartii*).

TABLE 1

Agronomic comparisons of CG4NU15 with LH59 and LH82.

|  | CG4NU15 | LH59 | LH82 | Locations |
|---|---|---|---|---|
| Number of 80000 kernel units per hectare | 126.0 | 143.3 | 49.4 | 6 |
| Percent of round kernels | 73.6 | 25.0 | 21.1 | 4 |
| Percent of large kernels | 68.7 | 61.8 | 1.6 | 4 |
| Percent of medium kernels | 26.3 | 31.6 | 12.6 | 4 |
| Percent of small kernels | 5.1 | 6.8 | 86 | 4 |
| Percent of discard kernels | 3.7 | 2.1 | 52.7 | 4 |
| Kernels per kilogram | 3454 | 3551 | 4457 | 4 |
| First pollen (days) | 70.8 | 69.3 | 68.7 | 6 |
| Mid pollen (days) | 72.6 | 71.2 | 70.6 | 6 |
| Mid pollen (heat units) | 1482 | 1460 | 1428 | 6 |
| First silk (days) | 72.7 | 70.7 | 69.1 | 6 |
| Mid silk (days) | 74.6 | 73.7 | 71 | 6 |
| Mid silk (heat units) | 1526 | 1498 | 1438 | 6 |
| Plant height cm. | 170 | 155 | 140 | 4 |
| Ear height cm. | 79 | 66 | 58 | 4 |

CG4NU15 is relatively unproductive as a seed parent, and produces predominantly large round seed, limiting its use as a seed line. Table 1 compares CG4NU15 with LH59 and LH82 for production and agronomic traits. While not closely related by pedigree to these lines, CG4NU15 is expected to be used in a similar way to these inbreds to produce hybrids for commercial sale.

This invention is also directed to methods for producing a maize plant by crossing a first parent maize plant with a second parent maize plant wherein the first or second maize plant is an inbred maize plant from inbred CG4NU15. Further, both first and second parent maize plants may be from either inbred line CG4NU15. Thus, any methods using the inbred maize line CG4NU15 are part of the invention including backcrosses, hybrid breeding, and crosses to populations. Any plants produced using inbred maize line CG4NU15 as a parent are within the scope of this invention. The best use of the inbred maize line CG4NU15 is for the production of first generation ($F_1$) maize hybrid seeds which produce plants with superior characteristics, by crossing either CG4NU15 (either as a seed line or as a pollen line) to another, distinct inbred line, both for sale to growers to produce market grain, and for inbreeding and development of improved inbred lines by its proprietors. A second important use of this inbred line is for the production of inbred seed of CG4NU15, by crossing CG4NU15 with another plant of CG4NU15, or by directly self-pollinating a plant of CG4NU15.

As used herein, the term "plant" includes plant cells, plant protoplasts, plant cell of tissue culture from which maize plants can be regenerated, plant calli, plant clumps, and plant cells that are intact in plants or parts of plants such as pollen, flowers, kernels, ears, cobs, leaves, husks, stalks, and the like. Thus another aspect of this invention is to provide for cells which upon growth and differentiation produce the inbred line CG4NU15.

The results in Tables 2 compare CG4NU15 hybrids to other Ciba Seeds hybrids, both commercial and experimental. In each comparison, the hybrids have an inbred in common which is not CG4NU15. Each comparison shows the effect of substituting CG4NU15 for a different inbred; in this way, an idea of general combining ability of CG4NU15 relative to a range of other inbreds is obtained. The data were averaged across locations and replications and include experiments grown by Ciba Seeds maize research programs in 1992, 1993, 1994 and 1995.

Table 2a compares a CG4NU15 hybrid with a pre-commercial hybrid for Ciba Seeds. The general background of the common inbred is Stiff stalk. The data show that the CG4NU15 hybrid has the same yield and value as the pre-commercial, is drier, has better % erect stalks but worse push data, and has better ear retention. The overall value of the two hybrids is the same, and the CG4NU15 hybrid may be expected to be grown further north than the pre-commercial hybrid.

TABLE 2a

Comparison of CG4NU15 hybrid 1 with non-CG4NU15 hybrid 2. Hybrids 1 and 2 have a line of Stiff stalk background in common which is not CG4NU15.

| Hybrid | Value | Yield | Percent Moist | Test Wgt/bu | % Erect Stalks | % Erect Push | Root H Rating | Dropped Ears(%) | Pit Hgt Inches | Ear Hgt Inches |
|---|---|---|---|---|---|---|---|---|---|---|
| 1 | 398.5 | 167.47 | 17.76 | 56.36 | 96.88 | 70.13 | 1.76 | 0.03 | 97.98 | 42.83 |
| 2 | 397.4 | 170.06 | 19.04 | 56.32 | 95.51 | 82.87 | 1.47 | 0.23 | 96.91 | 42.47 |
| # locs. | 60 | 60 | 60 | 59 | 39 | 46 | 17 | 24 | 29 | 29 |
| LSD(0.01) | 15.15 | 6.32 | 0.44 | 0.70 | 1.52 | 7.04 | 0.64 | 0.31 | 1.79 | 1.60 |
| LSD(0.05) | 11.39 | 4.75 | 0.33 | 0.52 | 1.13 | 5.27 | 0.46 | 0.23 | 1.33 | 1.18 |
| LSD(0.10) | 9.51 | 3.97 | 0.28 | 0.44 | 0.94 | 4.39 | 0.38 | 0.19 | 1.10 | 0.98 |
| Diff.(2-1) | −1.13 | 2.59 | 1.28 | −0.04 | −1.37 | 12.74 | −0.29 | 0.19 | −1.07 | −0.36 |
| CG4NU15 hybrid is: | same | same | drier | same | better | worse | same | better | same | same |

Table 2b compares a CG4NU15 hybrid with a commercial hybrid for Ciba Seeds. The general background of the common inbred is Stiff Stalk. The CG4NU15 hybrid yields more, is drier, and provides better value for the grower. Its stalk quality is the same or better than the commercial hybrid, but the test weight of the grain is slightly less. It is a taller hybrid with higher ear placement.

TABLE 2b

Comparison of CG4NU15 hybrid 1 with non-CG4NU15 hybrid 2. Hybrids 1 and 2 have a line of Stiff stalk background in common which is not CG4NU15.

| Hybrid | Value | Yield | Percent Moist | Test Wgt/bu | % Erect Stalks | % Erect Push | Root H Rating | Dropped Ears(%) | Pit Hgt Inches | Ear Hgt Inches |
|---|---|---|---|---|---|---|---|---|---|---|
| 1 | 408.3 | 172.00 | 17.89 | 56.10 | 97.47 | 73.95 | 2.00 | 0.02 | 94.18 | 42.40 |
| 2 | 389.1 | 167.85 | 19.57 | 56.75 | 96.63 | 60.36 | 2.13 | 0.00 | 86.06 | 40.10 |
| # locs. | 59 | 59 | 59 | 57 | 45 | 43 | 16 | 35 | 25 | 25 |
| LSD(0.01) | 12.48 | 5.11 | 0.43 | 0.57 | 1.52 | 9.28 | 1.35 | 0.06 | 2.37 | 2.34 |
| LSD(0.05) | 9.38 | 3.84 | 0.32 | 0.43 | 1.14 | 6.94 | 0.98 | 0.05 | 1.75 | 1.73 |
| LSD(0.10) | 7.83 | 3.21 | 0.27 | 0.36 | 0.95 | 5.78 | 0.80 | 0.04 | 1.45 | 1.43 |
| Diff.(2-1) | −19.13 | −4.15 | 1.68 | 0.66 | −0.84 | −13.59 | 0.13 | −0.02 | −8.12 | −2.30 |
| CG4NU15 hybrid is: | better | better | drier | lighter | same | better | same | same | taller | higher eared |

Table 2c compares a CG4NU15 hybrid with a pre-commercial hybrid from Ciba Seeds. The general background of the common inbred is Stiff Stalk and Iodent. The CG4NU15 hybrid has better yield, value and overall agronomics, but is slightly wetter compared to the pre-commercial hybrid.

TABLE 2c

Comparison of CG4NU15 hybrid 1 with non-CG4NU15 hybrid 2. Hybrids 1 and 2 have a line of G39 and Iodent background in common which is not CG4NU15.

| Hybrid | Value | Yield | Percent Moist | Test Wgt/bu | % Erect Stalks | % Erect Push | Root H Rating | Dropped Ears(%) | Pit Hgt Inches | Ear Hgt Inches |
|---|---|---|---|---|---|---|---|---|---|---|
| 1 | 355.6 | 154.79 | 20.12 | 55.44 | 93.99 | 83.75 | 1.40 | 1.02 | 98.67 | 48.00 |
| 2 | 333.4 | 141.21 | 18.30 | 57.25 | 92.19 | 66.25 | 1.20 | 2.42 | 100.33 | 45.33 |
| # locs. | 19.00 | 19.00 | 19.00 | 15.00 | 18.00 | 8.00 | 5.00 | 12.00 | 3.00 | 3.00 |
| LSD(0.01) | 25.46 | 11.18 | 0.83 | 1.52 | 4.65 | 20.66 | 1.53 | 1.57 | 9.81 | 7.39 |
| LSD(0.05) | 19.19 | 8.42 | 0.62 | 1.14 | 3.50 | 15.32 | 1.11 | 1.18 | 6.78 | 5.08 |
| LSD(0.10) | 16.04 | 7.04 | 0.52 | 0.95 | 2.93 | 12.72 | 0.92 | 0.98 | 5.47 | 4.10 |
| Diff.(2-1) | −22.22 | −13.59 | −1.81 | 1.80 | −1.79 | −17.50 | −0.20 | 1.40 | 1.67 | −2.67 |
| CG4NU15 hybrid is: | better | better | wetter | lighter | same | better | same | better | same | same |

Table 2d compares a CG4NU15 hybrid with a commercial hybrid for Ciba Seeds. The background of the common inbred is Stiff Stalk. The CG4NU15 hybrid yields the same as the commercial hybrid, is drier and provides better value. The test weight of the grain is slightly less for the CG4NU15 hybrid. It is a taller hybrid with higher ear placement than the commercial hybrid.

TABLE 2d

Comparison of CG4NU15 hybrid 1 with non-CG4NU15 hybrid 2. Hybrids 1 and 2 have a line of Stiff stalk background in common which is not CG4NU15.

| Hybrid | Value | Yield | Percent Moist | Test Wgt/bu | % Erect Stalks | % Erect Push | Root H Rating | Dropped Ears(%) | Pit Hgt Inches | Ear Hgt Inches |
|---|---|---|---|---|---|---|---|---|---|---|
| 1 | 388.7 | 166.3 | 18.81 | 54.72 | 96.88 | 73.80 | 1.83 | 0.41 | 96.23 | 44.45 |
| 2 | 371.8 | 162.2 | 20.28 | 55.84 | 97.01 | 69.64 | 1.33 | 0.32 | 82.89 | 38.05 |
| # locs. | 32 | 32 | 32 | 30 | 30 | 16 | 6 | 29 | 11 | 11 |
| LSD(0.01) | 22.41 | 9.29 | 0.62 | 0.95 | 1.71 | 15.88 | 1.38 | 0.37 | 4.93 | 3.00 |
| LSD(0.05) | 16.66 | 6.90 | 0.46 | 0.71 | 1.27 | 11.49 | 0.88 | 0.28 | 3.46 | 2.11 |
| LSD(0.10) | 13.85 | 5.74 | 0.38 | 0.59 | 1.05 | 9.45 | 0.69 | 0.23 | 2.82 | 1.71 |
| Diff.(2-1) | −16.92 | −4.13 | 1.47 | 1.12 | 0.13 | −4.17 | −0.50 | −0.09 | −13.34 | −6.41 |
| CG4NU15 hybrid is: | better | same | drier | lighter | same | same | same | same | taller | higher eared |

Restriction fragment length polymorphisms were assessed in the source population of CG4NU15. Y01 X 217A was found to be heterozygous at thirty-nine loci (Table 3). Of these, thirty-eight loci have two variants in the source population and one has three variants. Using Allard's formula, this source material is capable of producing 824,633,720,832 distinct homozygous genotypes for the loci characterized, only one of which is CG4NU15. To put this into perspective, if all possible inbred genotypes (considering only the RFLP loci which have been evaluated) from this source population were to be grown at a commercial density, with each genotype represented by only one plant, nearly 13,000,000 hectares would be filled. It is evident that a person highly trained in the art could start with exactly the same source material, use the same breeding techniques, and develop a new maize inbred, but it would be extremely unlikely to be the same inbred as CG4NU15. Further, given sampling error and the necessity for testing across numerous environments, a skilled breeder can have no assurance that he will be able to develop a commercially usable inbred line at all from this or any other source population, let alone one which shows the distinct advantages of CG4NU15.

TABLE 3

Restriction fragment length polymorphisms of CG4NU15 and its parents.

| Probe | CG4NU15 | Y01 | 217A | Variants in source |
|---|---|---|---|---|
| B05.09 | CC | CC | EE | 2 |
| B05.71 | BB | BB | CC | 2 |
| B07.13 | BB | BG | BB | 2 |
| B07.71 | FF | FF | II | 2 |
| B15.21 | CC | AA | CC | 2 |
| B16.06 | FF | DD | FF | 2 |
| N053 | DD | DD | AA | 2 |
| N110 | CC | CC | AA | 2 |
| N223 | DD | FF | DD | 2 |
| N247 | EE | BB | EE | 2 |
| N256 | DD | DD | CC | 2 |
| N270 | CC | EE | CC | 2 |
| N280 | FF | JJ | FF | 2 |
| N284 | AA | AA | AC | 2 |
| N286 | EE | EE | BB | 2 |
| N295 | JJ | JJ | HH | 2 |
| N296 | GG | AG | HH | 3 |
| N421 | KK | KK | EE | 2 |
| N432 | DD | DD | NN | 2 |
| N446 | CC | AA | CC | 2 |
| N451 | BB | BB | EE | 2 |
| N457 | EE | EE | AA | 2 |

TABLE 3-continued

Restriction fragment length polymorphisms of CG4NU15 and its parents.

| Probe | CG4NU15 | Y01 | 217A | Variants in source |
|---|---|---|---|---|
| N560 | DD | EE | DD | 2 |
| N585 | HH | HH | FF | 2 |
| U019 | DD | CC | DD | 2 |
| U028 | DD | DD | BB | 2 |
| U032 | BB | FF | BB | 2 |
| U051 | GG | AA | GG | 2 |
| U057 | DF | DD | FF | 2 |
| U060 | AA | AA | CC | 2 |
| U062 | DD | DD | AA | 2 |
| U084 | DD | DD | AA | 2 |
| U089 | BB | BB | EE | 2 |
| U090 | BB | CC | BB | 2 |
| U095 | BB | BB | AA | 2 |
| U121 | JJ | BB | JJ | 2 |
| U136 | CC | EE | CC | 2 |
| U139 | FF | FF | CC | 2 |
| U157 | EE | EE | CC | 2 |

Seeds of inbred CG4NU15 have been placed on deposit at the American Type Culture Collection (ATCC), Rockville, Md., 20852, under deposit accession number 97476 on Mar. 13, 1996. Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred maize line designated CG4NU15 (ATCC Designation 97476).

2. A plant or plants of the inbred maize line designated CG4NU15 of claim 1.

3. Plant parts of the plant of claim 2.

4. The plant parts of claim 3 wherein the plant parts are pollen or seed.

5. Tissue culture of the plant of claim 2.

6. Tissue culture according to claim 5 comprising regenerable cells of a plant part selected from meristematic tissue, anthers, leaves, embryos, pollen, and protoplasts therefrom.

7. A maize plant regenerated from the regenerable cells of a tissue culture according to claim 6 having all of the physiological and morphological characteristics of inbred maize plant CG4NU15 (ATCC Designation 97476).

8. An inbred maize plant with all of the genetic, physiological and morphological characteristics of the inbred maize line designated CG4NU15 (ATCC Designation 97476).

9. A method for producing maize seed comprising crossing a first parent maize plant with a second parent maize plant wherein said first or second parent maize plant is the inbred maize plant having designation CG4NU15 (ATCC Designation 97476) and harvesting the seed produced thereby.

10. The method of claim 9, wherein said first and second parent maize plants are both from the inbred maize line designated CG4NU15.

11. A first generation ($F_1$) maize plant and seed thereof produced by the method of claim 9.

12. A first generation ($F_1$) maize plant and seed thereof produced by the method of claim 10.

13. A first generation ($F_1$) hybrid maize plant and seed thereof produced by crossing a first inbred female maize plant with a second inbred male maize plant, wherein said first or second parent maize plant is the inbred maize plant having the designation CG4NU15 (ATCC Designation 97476).

14. The hybrid maize plant and seed thereof of claim 13, wherein said inbred maize plant having the designation CG4NU15 is the female parent.

15. The hybrid maize plant and seed thereof of claim 13, wherein said inbred maize plant having the designation CG4NU15 is the male parent.

16. A method for producing first generation ($F_1$) hybrid maize seed comprising crossing a first inbred parent maize plant with a second inbred parent maize plant, wherein said first or second parent maize plant is the inbred maize plant having the designation CG4NU15 (ATCC Designation 97476), and harvesting the $F_1$ hybrid seed produced thereby.

17. A first generation ($F_1$) hybrid maize plant and seed thereof produced by growing said hybrid maize seed of claim 16.

* * * * *